US008096983B2

(12) United States Patent
Uchino et al.

(10) Patent No.: US 8,096,983 B2
(45) Date of Patent: Jan. 17, 2012

(54) CONTINUOUS SUBCUTANEOUS INSULIN INFUSION THERAPY

(75) Inventors: Hiroshi Uchino, Bunkyo-ku (JP); Yasushi Tanaka, Bunkyo-ku (JP); Ryuzo Kawamori, Bunkyo-ku (JP)

(73) Assignee: Juntendo University, Tokyo (JP)

( * ) Notice: Subject to any disclaimer, the term of this patent is extended or adjusted under 35 U.S.C. 154(b) by 1082 days.

(21) Appl. No.: 11/817,966

(22) PCT Filed: Mar. 7, 2006

(86) PCT No.: PCT/JP2006/304307
§ 371 (c)(1),
(2), (4) Date: Nov. 30, 2007

(87) PCT Pub. No.: WO2006/095701
PCT Pub. Date: Sep. 14, 2006

(65) Prior Publication Data
US 2008/0119826 A1  May 22, 2008

(30) Foreign Application Priority Data
Mar. 7, 2005 (JP) .................................. 2005-062168

(51) Int. Cl.
*A61M 31/00* (2006.01)
(52) U.S. Cl. ......................................... 604/503; 604/66
(58) Field of Classification Search .................. 604/500, 604/502–504, 506–508, 65–67; 600/368
See application file for complete search history.

(56) References Cited

U.S. PATENT DOCUMENTS
6,572,542 B1   6/2003 Houben et al.
2002/0169365 A1  11/2002 Nakada et al.
2005/0027183 A1   2/2005 Sastre FOREIGN PATENT DOCUMENTS
EP   1 256 314 A1  11/2002
JP   2002 85556    3/2002
JP   2004 24699    1/2004
WO   WO 01/13786 A1  3/2001
WO   2004 006982   1/2004

OTHER PUBLICATIONS
Extended European Search Report issued Mar. 29, 2011, in Patent Application No. 06728676.5.
(Continued)

*Primary Examiner* — Kevin C Sirmons
*Assistant Examiner* — Catherine N Witczak
(74) *Attorney, Agent, or Firm* — Oblon, Spivak, McClelland, Maier & Neustadt, L.L.P.

(57) ABSTRACT

A mechanism for optimizing insulin infusion rate of a CSII pump for each patient. A continuous subcutaneous insulin infusion therapy uses a continuous subcutaneous insulin pump, which includes: determining a circadian variation curve representing sympathetic nerve activity and that represents parasympathetic nerve activity of a target patient; acquiring an inflection point of each of the circadian variation curves representing the two types of nerve activity; detecting a time that corresponds to the inflection point; and employing the time as a point at which the insulin infusion rate of the continuous subcutaneous insulin infusion pump is changed.

15 Claims, 4 Drawing Sheets

OTHER PUBLICATIONS

Hiroshi Uchino, et al., "Novel Approach to Identify Noctual Basal Insulin Infusion Rate in Type 1 Diabetes Using Continuous Subcutaneous Insulin Infusion: Sympatovagal Balance and Basal Insulin Infusion Rate", Diabetespro, 65$^{th}$ Annual Meeting of the American-Diabetes-Association, http://professional.diabetes.org./Abstracts_Display.aspx?TYP=1&CID=51827, XP 2623941, Jun. 10-14, 2005, 1 page.

A.G. Glasmacher, et al., "Differences in Circadian Insulin Requirements", Aktuelle Endokrinologie Und Stoffwechsel, vol. 12, No. 3, XP 9139588, Jan. 1, 1991, pp. 203-209 (with English Abstract).

CONTINUOUS SUBCUTANEOUS INSULIN INFUSION THERAPY

TECHNICAL FIELD

The present invention relates to a method for modulating the insulin infusion rate so as to maintain an optimum blood glucose level in continuous subcutaneous insulin infusion (CSII) therapy.

BACKGROUND ART

Diabetes is classified into type 1 diabetes, type 2 diabetes, diabetes in pregnancy, and other types. In a certain stage of type 1 diabetes and type 2 diabetes, insulin infusion therapy is effective. Such an insulin therapy is essential particularly for type 1 diabetes.

In healthy people, basal insulin secretion and additional insulin secretion occur. The basal secretion momentarily varies in level with providing a sufficient amount over 24 hours for maintaining homeostasis in the body, while the additional insulin secretion matches a sufficient amount of insulin in response to ingestion of nutrients and other physiological conditions. In order to bring blood insulin concentration of patients with insulin deficient diabetes to that of healthy people, a predetermined amount of insulin must be continuously infused to the patients, and moreover, when necessary, a required amount of insulin must be additionally infused. CSII is a technique developed for realizing continuous infusion of insulin, and through this technique, insulin is continuously infused to diabetes patients by means of an insulin pump for CSII (Non-Patent Document 1). More than 500,000 type 1 diabetes patients in worldwide are now receive this therapy every day. For maintaining the blood glucose level of the diabetes patients at that of healthy people, it is important that the insulin infusion rate of a CSII pump be adjusted to a predetermined level required for individual patients.

DISCLOSURE OF THE INVENTION

Problems to be Solved by the Invention

However, there has not been established algorithm for optimizing the temporal change in insulin infusion rate of a CSII pump for individual patients, and in general the infusion rate is empirically determined by the attending physician.

Thus, an object of the present invention is to provide means for optimizing the insulin infusion rate of a CSII pump for each patient.

Means for Solving the Problems

In view of the foregoing, the present inventors have attempted to make use of information regarding to cardiac autonomic nerve activity, which generally relates to diseases in the fields of neurology and cardiology, for the CSII therapy, and have found that the insulin infusion rate for a diabetes patient can be appropriately determined to thereby provide an optimized control of blood glucose level of the patient by changing the insulin infusion rate at inflection points of a circadian variation curve representing sympathetic nerve activity and parasympathetic nerve activity of the patient obtained through the microneurogram method or through power spectral analysis of heart rate variability observed by means of a digital Holter's electrocardiograph. The present invention has been accomplished on the basis of this finding.

Accordingly, the present invention provides a continuous subcutaneous insulin infusion therapy using a continuous subcutaneous insulin pump, which comprises determining a circadian variation curve representing sympathetic nerve activity and a circadian variation curve representing parasympathetic nerve activity of a target patient;

acquiring an inflection point of the circadian variation curves each representing the sympathetic nerve activity and an inflection point of the circadian variation curve representing the parasympathetic nerve activity;

detecting a time which corresponds to the inflection point; and employing the time as a point at which an insulin infusion rate of the continuous subcutaneous insulin infusion pump is changed.

The present invention also provides a method for operating a continuous subcutaneous insulin infusion pump, which comprises employing a circadian variation curve representing sympathetic nerve activity and a circadian variation curve representing parasympathetic nerve activity derived from a target patient for acquiring an inflection point of the circadian variation curve representing the sympathetic nerve activity and an inflection point of the circadian variation curve representing the parasympathetic nerve activity;

detecting a time which corresponds to the inflection point; and employing the time as a point at which an insulin infusion rate of the continuous subcutaneous insulin infusion pump is changed.

The present invention also provides an apparatus for continuous subcutaneous insulin infusion therapy, which comprises a means for determining a circadian variation curve representing sympathetic nerve activity and a circadian variation curve representing parasympathetic nerve activity of a target patient using a probe attached to a target patient;

an operational processing unit; and a continuous subcutaneous insulin infusion pump, wherein the operational processing unit has a means for detecting a time which corresponds to an inflection point of the circadian variation curve representing the sympathetic nerve activity and an inflection point of the circadian variation curve representing the parasympathetic nerve activity to employ the time as a point at which an insulin infusion rate of the continuous subcutaneous insulin infusion pump is changed.

EFFECTS OF THE INVENTION

According to the continuous subcutaneous insulin infusion therapy of the present invention, the insulin infusion rate can be changed and controlled at a time which corresponds to an inflection point of a variation curve representing sympathetic nerve activity and a variation curve representing parasympathetic nerve activity, which is acquired from the nerve activity data obtained by means of a portable cardiograph or a similar apparatus, whereby the insulin infusion rate can be controlled in accordance with the condition of each, to thereby optimize blood glucose level.

BEST MODES FOR CARRYING OUT THE INVENTION

The continuous subcutaneous insulin infusion therapy of the present invention is carried out by means of a continuous subcutaneous insulin infusion pump. The continuous subcutaneous insulin infusion pump is an apparatus having an insulin reservoir and a pump for infusion of insulin and is employed for continuously and subcutaneously infusing insulin to a via an infusion tube. The apparatus generally includes therein a clock and a program which allows the infusion rate to be changed at predetermined intervals. In currently commercially available models of such an apparatus, modulation of the insulin infusion rate over time is performed with respect to each patient by physician's personal instructions. At the meal time, the program allows each patient to be infused an additional amount of insulin.

In the method of the present invention, circadian variation curves, each representing sympathetic nerve activity and parasympathetic nerve activity in a target patient, are determined using a probe attached to the patient. These circadian variation curves of the two types of nerve activity may be determined by direct measurement of sympathetic nerve activity and parasympathetic nerve activity. Alternatively, other data may be obtained from the patient, and processed to transform it into circadian variation curves representing sympathetic nerve activity and parasympathetic nerve activity, respectively.

An exemplary means for directly determining these circadian variation curves of the two types of nerve activity includes microneurography (micro-needle electrode method) using a probe attached to a patient. The "microneurography" is an apparatus for measuring and recording sympathetic nerve activity, which is important for regulation of body functions, as an electric signal from nerves in the human skeletal muscle using a metallic microelectrode having an about 11 tip. In general, the apparatus is not suited for long-term measurement, but can directly analyze the autonomic nerve present in the skeletal muscle. Through the apparatus, sympathetic nervous activity can be measured directly from the peripheral nerve system.

An exemplary means for indirectly determining these circadian variation curves of the two types of nerve activity includes a means for conducting power spectral analysis of heart rate variability using a heart rate data included in an electrocardiographic data obtained from a signal detected by an electrode attached to a patient. Through the power spectral analysis of the heart rate variability, circadian variation curves representing sympathetic nerve activity and parasympathetic nerve activity are extracted. From the viewpoint of simplicity, the means for determining the variation curves from electrocardiographic data is preferred. The means for extracting the variation curves representing the two types of nerve activities from electrocardiographic data is included in the operational processing unit.

The means for determining, from electrocardiographic data, circadian variation curves representing the two types of nerve activity preferably includes a portable electrocardiograph for obtaining electrocardiographic data via a probe attached to a patient; and a means in the operational process unit, for extracting circadian variation curves each representing sympathetic nerve activity and parasympathetic nerve activity through power spectral analysis of heart rate variability which conducted using heart rate data included in the obtained electrocardiographic data.

The portable electrocardiograph employed in the present invention is a so-called digital Holter's electrocardiograph and preferably includes a probe (electrode) attached to a patient, an operational process unit, and a memory unit. No particular limitation is imposed on the type of the digital Holter's electrocardiograph, so long as it allows long-term electrocardiographic data measurement and storing. For example, the digital Holter's electrocardiograph can store electrocardiographic data for 24 hours or longer, preferably 24 to 1,680 hours, and has a sensitivity of 1 mV/512 and 0.1 to 20 Hz±3 dB and a measurement window of 250 Hz. R-R intervals measured by an electrocardiograph are employed as basic data for determining heart rate variability.

Alternatively, the portable electrocardiograph may be incorporated in the continuous subcutaneous insulin infusion pump. In other words, an operational process unit and a memory unit, which are functional elements of the portable electrocardiograph, can be incorporated in the continuous subcutaneous insulin infusion pump. The electrode may also serve as an insulin infusion tube.

The heart rate variability determined from R-R intervals of electrocardiographic data is transformed into circadian variation curves representing the two types of nerve activities, through power spectral analysis of the heart rate variability. Power spectral analysis of heart rate variability, also called frequency domain analysis, is a widely known mathematical technique to detect periodical characteristics of temporal heart rate variability having fractal characteristics (complexity). In power spectral analysis, all periodical characteristics of the temporal data of R-R intervals obtained by an electrocardiograph are extracted (spectral analysis), and a plurality of modes (peaks emerging in spectral analysis) obtained through the spectral analysis are reduced to the original temporal data, whereby a periodic component of the temporal data is selectively extracted (i.e., power spectral analysis). Among power spectral analysis methods, the MemCalc method is preferably employed. Through power spectral analysis, heart rate variability is divided into four frequency domains: LF (low-frequency domain: 0.04 to 0.15 Hz), HF (high-frequency domain: 0.15 to 0.40 Hz), VLF (very low-frequency domain: 0.003 to 0.04 Hz), and ULF (ultralow-frequency domain: <0.003 Hz). The HF component serves as an index for cardiac-parasympathetic nerve activity and LF and the LF/HF ratio serve as an index for cardiac-sympathetic nerve activity.

Figure 1:
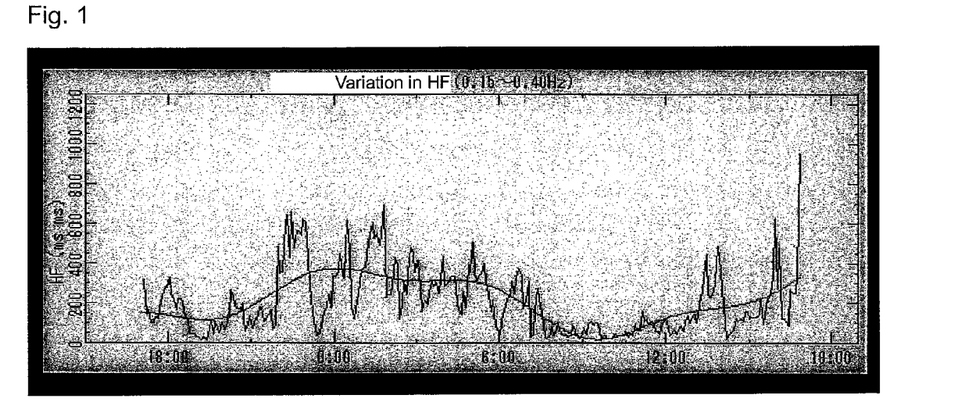
FIG. 1 A chart showing circadian variation of parasympathetic nerve activity measured by means of a digital Holter's electrocardiograph.
Figure 2:
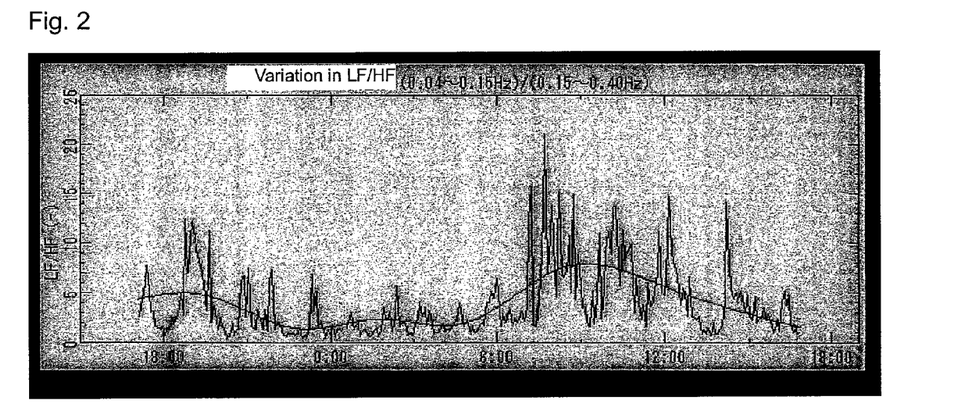
FIG. 2 A chart showing circadian variation of sympathetic nerve activity measured by means of a digital Holter's electrocardiograph.

Through power spectral analysis of heart rate variability, a circadian variation curve representing sympathetic nerve activity (LF or LF/HF ratio) and a circadian variation curve representing parasympathetic nerve activity (HF) are extracted. FIG. 2 shows an exemplary sympathetic nerve activity component (LF/HF ratio), and FIG. 1 shows an exemplary parasympathetic nerve activity component (HF). Gentle curves (average) shown in FIGS. 1 and 2 (lateral axis: time)

indicate that sympathetic nerve activity is high in the daytime and low at night/midnight, while vice versa in parasympathetic nerve activity.

According to the continuous subcutaneous insulin infusion therapy of the present invention, an inflection point of each of the two circadian variation curves representing the two types of nerve activity is determined to detect a time which corresponds to the inflection point. The procedure is carried out in the operational process unit. The operational process unit may be incorporated in a continuous subcutaneous insulin infusion pump, or the procedure may be carried out by another computer.

Figure 3:
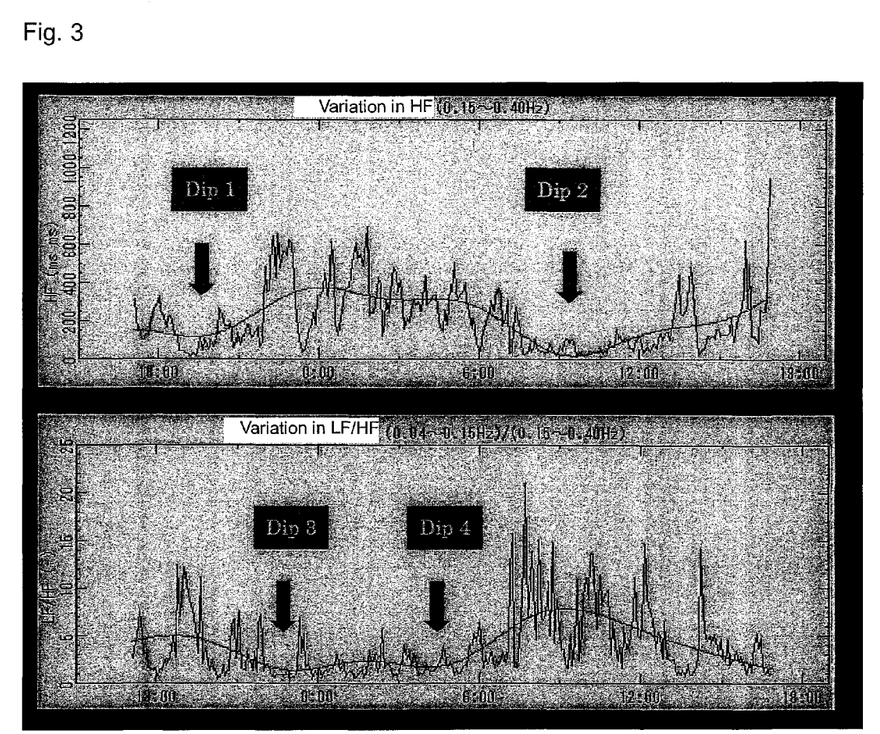
FIG. 3 A chart showing inflection points of circadian variation curves each representing sympathetic nerve activity and parasympathetic nerve activity.

In one embodiment, an inflection point of each of the two circadian variation curves representing the two types of nerve activity is determined to detect a time which corresponds to the inflection point. Exemplary determination procedure is illustrated in FIG. 3. In FIG. 3, the upper graph shows a circadian variation curve representing parasympathetic nerve activity, and the lower graph shows a circadian variation curve representing sympathetic nerve activity. Dip 1 to Dip 4 in FIG. 3 denote inflection points. At the times which correspond to the inflection points, modifications in sympathetic nerve activity and parasympathetic nerve activity are reciprocally altered. According to the present invention, each of the times is employed as a point in time at which the insulin infusion rate is changed. Thus, the insulin infusion rate may be changed at a time which corresponds to the inflection point. Specifically, when sympathetic nerve activity is predominant, insulin infusion rate may be increased, whereas when parasympathetic nerve activity is predominant and sympathetic nerve activity may be suppressed, insulin infusion rate is decreased.

Figure 4:
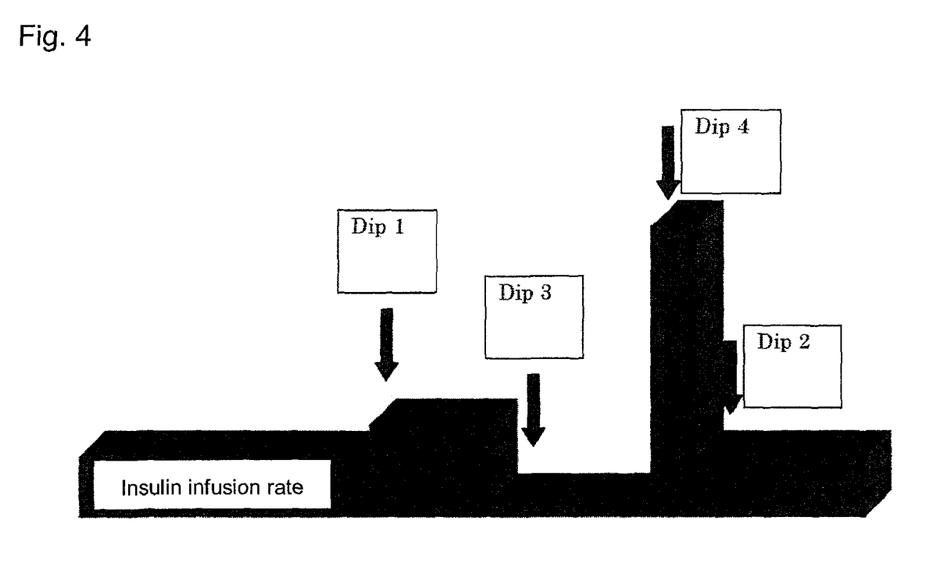
FIG. 4 A diagram showing insulin infusion rate and points at which the infusion rate is changed.

More specifically, two points in time (Dip 1 and Dip 2) are detected which corresponding to two inflection points on the circadian variation curve representing parasympathetic nerve activity (FIG. 3), and two points in time (Dip 3 and Dip 4) are detected which corresponding to two inflection points on the circadian variation curve representing sympathetic nerve activity (FIG. 3). In a preferred manner, insulin infusion rate is increased at Dip 1, decreased at Dip 3, increased at Dip 4, and decreased at Dip 2 (FIG. 4). In FIG. 4, in a preferred mode, when the insulin infusion rate during the period from Dip 2 to Dip 1 is 1 (i.e., the insulin infusion rate at Dip 2 is 1), the infusion rate is increased to 1.1 to 1.5 at Dip 1, decreased to 0.1 to 0.2 at Dip 3, increased to 2 to 4 at Dip 4, and decreased to 1 at Dip 2. The infusion rate may be determined with respect to each patient within the above ranges.

Once the time which corresponds to the inflection point was detected, insulin infusion rate may be changed manually by a patient or automatically. In the case where the patient manually changes the infusion rate, the continuous subcutaneous insulin infusion pump may be equipped with a means for notifying the patient of the detection of the time which corresponds to an inflection point (e.g., a buzzer, a vibrator, a blinking light, or a transmitter to a mobile phone.

When the insulin infusion rate is changed automatically, the continuous subcutaneous insulin infusion pump is equipped with an apparatus for changing insulin infusion rate when the time which corresponds to the inflection point has been detected.

Generally, the times which correspond to inflection points on the circadian curve representing autonomic nerve activity are not greatly changed day by day. Therefore, once the inflection time points has been determined, the times of changing insulin infusion rate may be predetermined in accordance with the time points, and patients themselves are not required to input new data every day to the continuous subcutaneous insulin infusion pump. Preferably, the times corresponding the inflection points and insulin infusion rate are predetermined by physician's instructions on the basis of the data stored in the memory unit.

The continuous subcutaneous insulin infusion pump includes a time-predetermining device and an insulin infusion pump. The times can be changed by users without any limitation. For example, even when a user has predetermined the infusion rate during the period from 3 AM to 7 AM to be 0.3 mL/h, the rate is not automatically programmed, and the user must input the data when and how much insulin is to be infused in accordance with a timer of the device. The insulin infusion pump generally contains 3 mL of insulin, and feeds insulin to a tube, which connecting the inside of a patient and the insulin pump, correctly at a specified infusion rate.

Thus, when the infusion program is predetermined for each patient such that the insulin infusion rate is changed at the times which correspond to the inflection points determined by the operational process unit, the blood glucose level of the patient can be controlled to the same level as that of healthy people.

EXAMPLES

The present invention will be described in more detail hereinafter by way of examples, which should not be construed as limiting the invention thereto.

Example 1

An apparatus for the continuous subcutaneous insulin infusion therapy was fabricated from a digital Holter's electrocardiograph (AC301, product of GMS) including a program for power spectral analysis of heart rate variability and a continuous subcutaneous insulin infusion pump (8100, product of TOP). The program for power spectral analysis of heart rate variability is included in the operational process unit of the digital Holter's electrocardiograph. The electrocardiograph can measure and store electrocardiographic data for maximum 1,680 hours at a sensitivity of 1 mV/512 and 0.1 to 20 Hz±3 dB with a measurement window of 250 Hz.

FIG. 1 shows a parasympathetic nerve activity component from a type 1 diabetes patient obtained by means of the apparatus for the continuous subcutaneous insulin infusion therapy of the invention, and FIG. 2 shows a sympathetic nerve activity component from the same patient. As shown in FIGS. 1 and 2, sympathetic nerve activity tends to be high in the day time and low at night and midnight, while vice versa in parasympathetic nerve activity. Inflection points of each of the circadian variation curves representing the nerve activities were determined. FIG. 3 shows the results. In FIG. 3, Dip 1 to Dip 4 denote inflection points.

The times which correspond to the inflection points on the curves were determined by means of the memory unit of the digital electrocardiograph. The CSII program was set such that insulin infusion rate was changed at the times which correspond to the inflection points. In the case of this patient, the insulin infusion rate was adjusted to 0.7 mL/h from Dip 1 to Dip 3, 0.1 mL/h from Dip 3 to Dip 4, 1.5 mL/h from Dip 4 to Dip 2, and 0.4 mL/h from Dip 2 to Dip 1 (FIG. 4). As a result, the blood glucose level of this patient was able to be controlled at the same level as that of healthy people.

Figure 5:
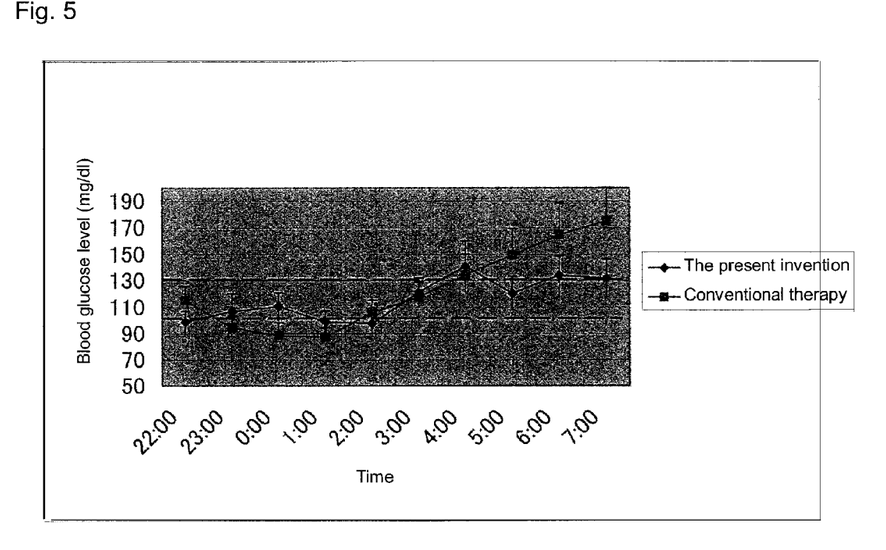
FIG. 5 A graph showing a difference in nocturnal variation of blood glucose level between a type 1 diabetes patient subjected to the therapy of the present invention and that subjected to a conventional therapy.

Since the nocturnal blood glucose level of type 1 diabetes patients does not depend on food intake and physical exercise, the blood glucose level can be stabilized through a correctly modulated basal insulin infusion rate over time. FIG. 5 shows the difference in nocturnal blood glucose level between a type 1 diabetes patient subjected to the therapy of the present invention and that subjected to a conventional therapy. In the conventional therapy, since blood glucose level decreases at midnight, the insulin infusion rate cannot be increased from the level of midnight. Thus, the blood glucose level gradually increases to the next morning. In contrast, according to the present invention, insulin infusion rate is synchronized with the aforementioned inflection points of individual patients, and nocturnal insulin infusion rate can be appropriately regulated. Therefore, nocturnal hypoglycemia can be prevented and hyperglycemia in the next morning can be treated. In FIG. 5, the dashed lines denote desired blood glucose levels of type 1 diabetes patients.

The invention claimed is:

1. A continuous subcutaneous insulin infusion therapy using a continuous subcutaneous insulin pump, which comprises:
   determining a circadian variation curve representing sympathetic nerve activity and a circadian variation curve representing parasympathetic nerve activity of a target patient;
   acquiring inflection points of the circadian variation curve representing the sympathetic nerve activity and inflection points of the circadian variation curve representing the parasympathetic nerve activity;
   detecting times which correspond to the inflection points; and
   employing said times as points at which an insulin infusion rate of the continuous subcutaneous insulin infusion pump is changed.

2. The continuous subcutaneous insulin infusion therapy as described in claim 1, wherein a means for determining the circadian variation curve of the sympathetic nerve activity and the circadian variation curve representing parasympathetic nerve activity is (1) a microneurogram method, or (2) a method comprising: conducting a power spectral analysis of heart rate variability using a heart rate data included in an electrocardiographic data obtained from a signal detected with an electrode attached to the patient; and extracting the circadian variation curve representing the sympathetic nerve activity and the circadian variation curve representing the parasympathetic nerve activity through the power spectral analysis of heart rate variability.

3. The continuous subcutaneous insulin infusion therapy as described in claim 1, further comprising:
   detecting two time points (Dip 1 and Dip 2) each corresponding to the inflection points of the circadian variation curve representing the parasympathetic nerve activity, and two time points (Dip 3 and Dip 4) each corresponding to the inflection points of the circadian variation curve representing the sympathetic nerve activity,
   wherein the insulin infusion rate is increased at Dip 1, decreased at Dip 3, increased at Dip 4, and decreased at Dip 2.

4. The continuous subcutaneous insulin infusion therapy as described in claim 1, wherein the patient is notified of detection of a time which corresponds to an inflection point.

5. The continuous subcutaneous insulin infusion therapy as described in claim 1, which further comprises a means for automatically changing the insulin infusion rate in response to detection of a time which corresponds to an inflection point.

6. A method for operating a continuous subcutaneous insulin infusion pump, which comprises:
   employing a circadian variation curve representing sympathetic nerve activity and a circadian variation curve representing parasympathetic nerve activity derived from a target patient for acquiring inflection points of the circadian variation curve representing the sympathetic nerve activity and inflection points of the circadian variation curve representing the parasympathetic nerve activity;
   detecting times which correspond to the inflection points; and
   employing said times as points at which an insulin infusion rate of the continuous subcutaneous insulin infusion pump is changed.

7. The method for operating a continuous subcutaneous insulin infusion pump as described in claim 6, wherein a means for determining the circadian variation curve of the sympathetic nerve activity and the circadian variation curve representing parasympathetic nerve activity is (1) a microneurogram method, or (2) a method comprising: conducting a power spectral analysis of heart rate variability using a heart rate data included in an electrocardiographic data obtained from a signal detected with an electrode attached to the patient; and extracting the circadian variation curve representing the sympathetic nerve activity and the circadian variation curve representing the parasympathetic nerve through the power spectral analysis of heart rate variability.

8. The method for operating a continuous subcutaneous insulin infusion pump as described in claim 6, further comprising:
   detecting two time points (Dip 1 and Dip 2) each corresponding to the inflection points of the circadian variation curve representing the parasympathetic nerve activity, and two time points (Dip 3 and Dip 4) each corresponding to the inflection points of the circadian variation curve representing sympathetic nerve activity,
   wherein the insulin infusion rate is increased at Dip 1, decreased at Dip 3, increased at Dip 4, and decreased at Dip 2.

9. The method for operating a continuous subcutaneous insulin infusion pump as described in claim 6, which further comprises a means for notifying the patient of detection of a time which corresponds to an inflection point.

10. The method for operating a continuous subcutaneous insulin infusion pump as described in claim 6, which further comprises a means for automatically changing the insulin infusion rate in response to detection of a time which corresponds to an inflection point.

11. An apparatus for continuous subcutaneous insulin infusion therapy, which comprises:
    a means for determining a circadian variation curve representing sympathetic nerve activity and a circadian variation curve representing parasympathetic nerve activity of a target patient using a probe attached to a target patient;
    an operational processing unit; and
    a continuous subcutaneous insulin infusion pump,
    wherein the operational processing unit has a means for detecting times which correspond to inflection points of the circadian variation curves representing the sympathetic nerve activity and inflection points of the circadian variation curve representing parasympathetic nerve activity to employ said times as points at which an insulin infusion rate of the continuous subcutaneous insulin infusion pump is changed.

12. The apparatus for continuous subcutaneous insulin infusion therapy as described in claim 11, wherein the means for determining the circadian variation curve representing the sympathetic nerve activity and the circadian variation curve representing the parasympathetic nerve activity is (1) a microneurogram for directly detecting the circadian variation curve representing the sympathetic nerve activity and the circadian variation curve representing the parasympathetic nerve activity of the target patient using a probe attached to the patient, or (2) a means comprising: conducting a power spectral analysis of heart rate variability using a portable electrocardiograph for obtaining an electrocardiographic data via a probe attached to the patient and a heart rate data included in the obtained electrocardiographic data in the operational processing unit; and extracting the circadian variation curve representing the sympathetic nerve activity and the circadian variation curve representing the parasympathetic nerve activity through the power spectral analysis of heart rate variability.

13. The apparatus for continuous subcutaneous insulin infusion therapy as described in claim 11, further comprising:
   detecting two time points (Dip 1 and Dip 2) each corresponding to the inflection points of the circadian variation curve representing the parasympathetic nerve activity, and two time points (Dip 3 and Dip 4) each corresponding to the inflection points of the circadian variation curve representing the sympathetic nerve activity,
   wherein the insulin infusion rate is increased at Dip 1, decreased at Dip 3, increased at Dip 4, and decreased at Dip 2.

14. The apparatus for continuous subcutaneous insulin infusion therapy as described in claim 11, which further comprises a means for notifying the patient of detection of a time which corresponds to an inflection point.

15. The apparatus for continuous subcutaneous insulin infusion therapy as described in claim 11, which further comprises a means for automatically changing the insulin infusion rate in response to the detection of a time which corresponds to an inflection point.

* * * * *